(12) United States Patent
Morinaga et al.

(10) Patent No.: US 7,456,118 B2
(45) Date of Patent: Nov. 25, 2008

(54) COLLAGEN SUBSTRATE, METHOD OF MANUFACTURING THE SAME, AND METHOD OF USING THE SAME

(75) Inventors: Yukihiro Morinaga, Osaka (JP); Ryosuke Kamimura, Osaka (JP); Kazuhisa Matsuda, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 11/481,098

(22) Filed: Jul. 6, 2006

(65) Prior Publication Data

US 2007/0009585 A1 Jan. 11, 2007

(30) Foreign Application Priority Data

Jul. 7, 2005 (JP) ............................. 2005-199218
Jul. 7, 2005 (JP) ............................. 2005-199344
Sep. 30, 2005 (JP) ............................. 2005-289300

(51) Int. Cl.
*D04H 1/00* (2006.01)
(52) U.S. Cl. ...................................... 442/369
(58) Field of Classification Search ................ 424/445, 424/444, 443; 604/289, 290; 442/369
See application file for complete search history.

(56) References Cited

U.S. PATENT DOCUMENTS

| 5,679,372 | A | 10/1997 | Shimuzu et al. | 424/445 |
| 6,977,231 | B1 | 12/2005 | Matsuda | 442/370 |
| 2003/0032601 | A1 | 2/2003 | Kreuter et al. | 514/21 |
| 2003/0114061 | A1 | 6/2003 | Matsuda et al. | 442/123 |

FOREIGN PATENT DOCUMENTS

| WO | 94/09831 | * 11/1994 |
| WO | 03/057072 A2 | 7/2003 |

* cited by examiner

*Primary Examiner*—Maryam Monshipouri
(74) *Attorney, Agent, or Firm*—Kubovcik & Kubovcik (57) ABSTRACT

In order to provide a substrate for medical applications, which may be freely elastically deformed depending on a shape of a defective portion or hemostasis portion in a living body, is biocompatible and suitable for tissue regeneration or cell proliferation, or hemostasis, and can be easily manufactured. A collagen substrate of the present invention includes a three-dimensional mesh formed of spun collagen filaments. Preferably, the collagen substrate of the present invention includes cotton formed of spun collagen filaments.

6 Claims, 9 Drawing Sheets

COLLAGEN SUBSTRATE, METHOD OF MANUFACTURING THE SAME, AND METHOD OF USING THE SAME

FIELD OF THE INVENTION

The present invention relates to a collagen substrate that includes collagen filaments. In particular, the present invention relates to a substrate for medical applications, such as various culture substrates including a substrate used in cell culture for transplantation in regenerative medicine, filling materials or prosthetic materials for promoting regenerative induction by filling defective sites in living bodies, and hemostats in the field of surgery or the like.

DESCRIPTION OF THE RELATED ART

In the field of regenerative medicine, original structures and functions of tissues or organs are regenerated and restored by providing an environment that serves as a scaffold where autologous cells can be proliferated with respect to tissues and organs in a body. In such regenerative medicine, as a substrate used for a scaffold to regenerate the defective organ or tissue, attention is focused on a substrate formed of a biodegradable material such as collagen. In particular, collagen is a principle protein of which a living body is constituted and is suitable in terms of biocompatibility, tissue regeneration, and cell proliferation. Meanwhile, in a case in which an intended cell is cultured in a living body using a substrate other than collagen, a preculture is sometimes required before in vivo culture in order to avoid disintegration or fluidization caused by decomposition of the substrate by means of a cell product, but the preculture may be omitted when using a collagen substrate. On the other hand, there is a problem in that collagen is difficult to process into a shape suitable for regeneration of various tissues and organs.

To produce a medical material of collagen, there are known a method of producing a sponge-like substrate by freeze-drying the resultant collagen solution; and a method of producing a fiber-like substrate by spinning a collagen solution by a wet spinning method (see, for example, U.S. Pat. No. 6,977,231 and U.S. Patent Publication No. 2003/0114061). Collagen is extracted from an animal such as a pig under a predetermined treatment such as acid or alkali. And then the extracted collagen is subjected to a pepsin treatment to remove antigenic expression site of collagen.

Meanwhile, in the field of surgery, a topical hemostat including collagen has attracted attention as a topical absorbable hemostat to inhibit bleeding by immediately forming thrombus. The hemostat including collagen has an advantage of causing very few allergic reactions. There is also an advantage that collagen itself has a hemostasis effect. Conventionally, a flocculent material formed of collagen filaments has been known as a topical absorbable hemostat including collagen (see U.S. Pat. No. 5,679,372).

BRIEF SUMMARY OF THE INVENTION

However, a medical material obtained by the above-described production method includes a two-dimensional material referred to as "nonwoven fabric", or a sponge-like material. While the nonwoven fabric of course has a thickness, it is used only as a substrate that extends in a two-dimensional direction. Therefore, it is preferable to use the nonwoven fabric as a substrate to regenerate a tubular or membrane-like tissue such as a blood vessel or an esophagus, while it is not preferable to use the nonwoven fabric as a three-dimensional substrate of a steric tissue or organ, for example, to use it to culture osteocytes in a living body by filling the substrate as a filing into a defective portion in the bone.

Meanwhile, for increasing strength of a nonwoven fabric, a binding treatment is performed to bind collagen threads by spraying a collagen solution or a gelatin solution onto collagen threads that vertically and horizontally cross each other, so there is a problem in that many steps are required to finally yield a nonwoven fabric. In addition, the resultant nonwoven fabric has no stretchability, so in order to fit it to defective portions having various shapes, it is necessary to cut the nonwoven fabric.

On the other hand, a sponge-like substrate may be used as a three-dimensional substrate of a steric tissue or organ, but it is impossible to elastically deform the substrate like a so-called sponge. That is, the sponge-like substrate is manufactured as a porous substrate by freeze-drying a collagen solution, so it has a disadvantage of having weak physical strength. Meanwhile, when a predetermined compression force is applied to a sponge-like collagen substrate, pores thereof are destroyed and deformed by the compression, and the destroyed pores are not restored even if the compression force is removed. Further, it is difficult to produce a substrate having desired strength against a compression force that is high enough to cause deformation. Moreover, the pores of the above-described sponge-like substrate are formed as isolated cells, so there are problems in that it is difficult to continuously proliferate cells between the cells and that it is difficult for the cells to grow.

Meanwhile, a flocculent product formed of collagen fibers, which is used as a hemostat, is obtained by dispersing collagen fibers each having a length of 3 to 70 mm by an air blower, followed by a heat treatment. There is a problem in that such a product including a plurality of collagen fibers having relatively short lengths is difficult to handle because the collagen fibers are easy to loosen from a mass of the flocculent product. The problem of loosening is more significant in the case where the flocculent product is particularly larger or in the case that the blood pressure of a site where bleeding is stopped, i.e., the blood pressure of a wound, is higher. For example, in filling a site where bleeding is to be stopped with the above-described flocculent product formed of collagen fibers, there is a problem in that the product is difficult to handle because the flocculent product adheres to the fingertips, tweezers, or the like to which blood or body fluid is added, resulting in loosening, so it is difficult to fill the site where bleeding is to be stopped with an appropriate amount of the flocculent product.

The present invention has been made in view of the above-mentioned problems, and an object of the present invention is to provide a substrate for medical application that is biocompatible and suitable for tissue regeneration or cell culture and that can be easily obtained.

Meanwhile, another purpose of the present invention is to provide a collagen flocculent product that can be freely elastically deformed depending on the shape of a defective portion or hemostasis portion in a living body.

(1) A collagen substrate according to the present invention comprises a three-dimensional mesh formed of spun collagen filaments.

(2) Further, the mesh may be obtained by drying and/or crosslinking a three-dimensional structure formed by discharging a collagen solution in a bath.

(3) Further, the mesh may be a cotton-like substrate.

(4) Further, the cotton-like substrate may include:
non-adhered contact sites where the collagen filaments contact and do not adhere to each other; and adhered contact sites where the collagen filaments adhere to each other.

(5) Further, the adhered contact sites may be formed by crosslinking.

(6) Further, the collagen filaments may be crosslinked after wet spinning.

(7) Further, the crosslinking may be thermal dehydration crosslinking.

(8) Further, the cotton-like substrate may be obtained by twining the collagen filaments in a solution.

(9) Further, the solution may be a neutralizing solution.

(10) Further, the collagen filaments preferably have lengths of 100 mm or more.

(11) Further, the collagen filaments preferably have lengths in a range of from 100 mm to 1,000,000 mm.

(12) Further, the collagen filaments preferably have diameters in a range of from 3 μm to 100 μm.

(13) A method of producing a collagen substrate according to the present invention includes as a forming step, spinning of collagen filaments into a three-dimensional mesh.

(14) Further, the method may include:
a discharging step of forming a three-dimensional structure by discharging a collagen solution in a bath; and
a drying step of drying and/or crosslinking the three-dimensional structure.

(15) Further, the method may include:
a spinning step of spinning collagen into collagen filaments; and
a cotton-forming step of producing a cotton-like substrate by twining the collagen filaments.

(16) Further, the cotton-forming step may be performed in a neutralizing solution used in the spinning step.

(17) Further, crosslinking may be performed after the cotton-forming step.

(18) Further, a method of using a collagen substrate includes using the collagen substrate described above as a hemostat.

(19) Further, a method of using a collagen substrate according to the present invention includes use of the collagen substrate described above as a culture substrate.

(20) Further, the culture substrate is formed into a desired shape of a human part.

(21) Further, a method of using a collagen substrate according to the present invention includes use of the collagen substrate described above as a filling material.

(22) Further, the filling material is formed into a desired shape of a human part.

In a collagen substrate according to the present invention, a medical substrate that maintains a three-dimensional shape is easily obtained, since the collagen filaments form a three-dimensional mesh.

Furthermore, in a collagen substrate according to the present invention, collagen filaments include a cotton-like substrate capable of being elastically deformed, so the collagen substrate may be deformed so as to reduce a total volume thereof depending on a compression force. Meanwhile, when the substrate is liberated from the compression force, an original shape is restored by elasticity of the collagen filaments. Therefore, there may be manufactured a substrate for medical application that is flexibly deformed depending on a shape of a defective portion or hemostasis portion in a living body. There may also be achieved a hemostat that has excellent handling ability without occurrence of loosening or the like in hemostasis and has a high hemostasis effect.

DETAILED DESCRIPTION OF THE INVENTION

Hereinafter, preferred embodiments of the present invention will be described.

A collagen substrate according to the present invention, comprises a three-dimensional mesh formed of spun collagen filaments.

The first example of the present invention is a three-dimensional mesh that is manufactured by drying and/or crosslinking a three-dimensional structure formed by discharging a collagen solution into a bath.

In the present invention, "a three-dimensional mesh" means having a three-dimensional structural scaffold which has continuous holes capable of cell growth in three dimensions.

The collagen to be used in the present invention is, for example, acid-solubilized collagen, alkali-solubilized collagen, or neutral-solubilized collagen, which includes one that has been subjected to a solubilization treatment by means of a protease such as pepsin or trypsin or a solubilization treatment by means of alkali. In particular, from a viewpoint of easy handling, acid solubilized collagen or alkali solubilized collagen is preferable, and atelocollagen which has been subjected to a treatment of removing a telopeptide, an antigenic determinant site of collagen, from collagen is more preferable.

An original source of collagen is not particularly limited, and there may be used one obtained from, for example, cows, pigs, birds, fish, rabbits, sheep, mice, and human beings, which can be obtained from skin, tendons, bones, cartilage, and organs of those living bodies by any of the extraction methods known in the art. The types of collagen, which are classified into types I, II, III, and the like, are not particularly limited, but it is preferable to use the same type of collagen as collagen which mainly constitutes a site to be regenerated. For example, to regenerate skin, bones, tendons, etc., type I is preferably used, to regenerate cartilage, etc., type II is preferably used, and to regenerate the skin, muscles, etc., type III is preferably used. Meanwhile, in terms of industrial handling, type I collagen is preferable.

The term "collagen filament" in the present invention means a thread that has been spun by any of various spinning methods. A step of spinning the collagen filament is referred to as a spinning step in the present invention. Examples of the spinning methods include a wet spinning method, dry spinning method, and melt spinning method. In particular, the wet spinning method is preferable because of easy production.

In the above-mentioned wet spinning method, a collagen solution is used. A solvent for solubilized collagen is not particularly limited as long as it solves the above-mentioned collagen, and examples thereof include: dilute acid solutions such as hydrochloric acid, acetic acid, and nitric acid; hydrophilic organic solvents such as ethanol, methanol, and acetone; and water. Meanwhile, such solvents may be used alone or two or more of them may be used in combination, but water is particularly preferable above all.

Meanwhile, the concentration of collagen in the collagen solution is not particularly limited as long as it allows spinning of collagen filaments by a predetermined spinning method. However, for example, in the case of spinning by the wet spinning method, the concentration is preferably about 0.5 to 30 w/w %, more preferably about 1 to 10 w/w %, and particularly preferably about 5 to 7 w/w %. Note that the wet spinning method is a production method of obtaining a collagen filament by continuously discharging a collagen solution from a nozzle into a bath filled with a solidifying liquid, followed by dehydration and solidification.

In the collagen substrate, the collagen filament is not required to be one continuous thread, but it is preferable to continuously spin the collagen filament into a nearly continuous thread. The length of one collagen filament may be a length enough to twine it later into a flocculent shape and to maintain the flocculent state by a further crosslinking, and specifically, the length is 100 mm or more, and preferably in the range of 100 to 1,000,000 mm.

In the wet spinning method, a bath into which a collagen solution is discharged is not particularly limited as long as it is filled with a solution capable of solidifying collagen, and for example, there may be used: an aqueous solution of an inorganic salt such as sodium sulfate, sodium chloride, ammonium sulfate, calcium chloride, or magnesium chloride; an inorganic salt-dissolved organic solvent prepared by dissolving or dispersing such inorganic salt in an alcohol or acetone; alcohols such as methanol, ethanol, isopropanol, or amyl alcohol; or ketones such as acetone or methyl ethyl ketone. Meanwhile, from a viewpoint of the strength of the collagen filament, the solidifying liquid is preferably an alcohol, and particularly preferably ethanol. Further, a water content in ethanol is preferably about 10% or less, more preferably about 5% or less, and particularly preferably about 1% or less from the viewpoint of the strength of the collagen filament.

To discharge a collagen solution into a bath, there may be used, for example, gear pumps, dispensers, and extruding apparatus that are known in the art, as long as they may continuously discharge a collagen solution from a head having a predetermined diameter. In particular, to yield collagen filaments having a uniform diameter, preferable is an apparatus having a uniform discharge rate of a collagen solution.

Meanwhile, the diameter of a head to discharge a collagen solution is fitted to the diameter of a desired collagen filament. The diameter of a collagen filament is determined in consideration of continuous spinning or flexibility of the collagen filament. In addition, a flocculent collagen substrate is conveniently used if it is modified into one that may be cut or torn off so as to suit the size of a defective portion in a living body. In view of this, the diameter of a collagen filament is 3 to 100 µm, preferably 5 to 75 µm, and it is preferable to adjust the diameter of the above-described head to nearly the same as the diameter of such the collagen filament.

Concretely, when the collagen solution is discharged into a bath, a head is moved at random along a horizontal plane. As a result, the collagen filament is formed into a three-dimensional structure at the bottom of the bath. In one case, a housing having a desired shape of a three-dimensional substrate of a steric tissue or organ is prepared. And the collagen solution is discharged at random into the housing. As a result, the collagen filament is formed into a desired shape of a three-dimensional structure at the bottom of the bath. This step is called a discharging step in the present invention.

The above-mentioned three-dimensional structure is picked up from the bath and dried (drying step). In this drying step, the three-dimensional structure includes an adhered contact site where the collagen filaments adhere to each other. The term "adhere" means a state where collagen filaments bind together to the extent that a shear stress between the collagen filaments may be generated. Examples of the form of the bond include a bond formed by a physical interaction, a bond formed by a chemical interaction, and a mechanical bond. In particular, from a viewpoint of bond strength, the bond formed by a chemical interaction is preferable, but the present invention is not limited thereto. Examples of a bond formed by a chemical interaction include a covalent bond, an ionic bond, a coordinate bond, and a hydrogen bond. In particular, from a viewpoint of bond strength, the covalent bond and ionic bond are preferable, and the covalent bond is most preferable, but the present invention is not limited thereto. Examples of a method of forming a covalent bond mainly include methods by crosslinking.

The crosslinking may be either a physical crosslinking method or a chemical crosslinking method. The physical crosslinking method is a crosslinking method including γ-ray, ultraviolet, electron beam, plasma, and thermal dehydration crosslinking. On the other hand, the chemical crosslinking method is a crosslinking method including use of aldehydes, epoxies, carbodiimides, isocyanates, a tannin treatment, a chromium treatment, etc. Meanwhile, in the chemical crosslinking method, solidification of a collagen solution and the crosslinking may be performed simultaneously by adding various crosslinking agents to a bath into which the collagen solution is discharged. In addition, when a collagen substrate is to be used as a substrate for in vivo culture or as a hemostat, the physical crosslinking method is preferably employed from a viewpoint of safety in implantation in a living body and cytotoxicity. Moreover, the physical crosslinking method is preferably, but not limited to, a thermal dehydration crosslinking method.

Such crosslinking makes a collagen filament insoluble, and the resultant product keeps its thread shape even if it is immersed in a solvent in which a solubilized collagen is dissolved. Meanwhile, in the case that the degree of crosslinking is low after the crosslinking, collagen is dissolved in a solvent again in a subsequent treatment, while in the case that the degree of crosslinking is high, a foreign-body reaction in a living body may be caused. In consideration of the strength of the collagen filament, when crosslinking is performed by a thermal dehydration crosslinking, thermal dehydration crosslinking is preferably performed at a temperature of about 110 to 140° C. for about 6 to 48 hours.

From a viewpoint of safeness of the substrate in the body, the crosslinked substrate is preferably neutralized in a neutralizing solution (neutralizing step). The neutralizing solution includes a solution for neutralizing a solvent of a collagen solution, and there may be used an acidic solution, alkaline solution, etc. depending on the pH of the substrate. The neutralization is preferably repeated at least twice while exchanging the neutralizing solution. In addition, as the neutralizing solution, a weak acidic solution or a weak alkaline solution are preferable from a viewpoint of maintaining a molecular structure of collagen, and for example, there may be used an aqueous sodium hydrogen carbonate solution, ammonia water, phosphate buffer, etc. Among them, an aqueous sodium hydrogen carbonate solution is preferable, but it is not required. Neutralization may suppress an inflammatory response in implanting a collagen substrate in a living body, so it is preferable.

From a viewpoint of strength of the substrate, the neutralized substrate may be crosslinked a second time. The crosslinking may use physical crosslinking and chemical crosslinking as well as the above-mentioned. To maintain neutralization of the collagen filament and to crosslink simply, thermal crosslinking is preferable. Meanwhile, in the case that thermal dehydration crosslinking is performed as a physical crosslinking method, it is preferably performed under reduced pressure at about 110 to 140° C. for about 6 to 48 hours. This treatment improves the strength of the collagen filaments, and maintains the three-dimensional structure having continuous holes by adhering the collagen filaments to each other. Note that the above-described substrate may be air-dried before or after the crosslinking.

As described above, a collagen substrate having a three-dimensional mesh can be obtained. With the collagen substrate according to the present invention, a medical substrate that maintains a three-dimensional shape is easily obtained, since the collagen filaments form a three-dimensional mesh. In in vitro culture, the cells can grow along in a three-dimensional scaffold. It is possible to use the three-dimensional as a filling material by molding the collagen substrate into the shape of a deficient or damaged tissue, such as an organ, bones and skin. Especially, if the collagen substrate is used as a filling material, regenerating a deficient or damaged tissue (in vitro culturing) is performed with stopping of bleeding by the collagen.

The second example of the present invention is a cotton-like three-dimensional substrate. The cotton-like substrate in the present invention is formed of at least one collagen filament and is a three-dimensional structure in which continuous holes are formed. The cotton-like substrate has an appearance similar to general cotton collected from raw cotton. Meanwhile, the cotton-like substrate may be elastically deformed so as to deform the shape and to reduce the volume. In addition, the cotton-like substrate has an ability to absorb liquid.

The collagen filaments of the second example are obtained by wet spinning (spinning step). The conditions in wet spinning, such as a solution in the bath, discharging apparatus and the diameter of a head, are mentioned above. However, the collagen filaments should be obtained by winding up on a core member, without forming the three-dimensional structure as in the first example.

After wet spinning, the collagen filaments are subjected to crosslinking (crosslinking step). The conditions of crosslinking are mentioned above.

The collagen filament is shaped into a cotton-like substrate. In the present invention, the shaping is referred to as a cotton-forming step. Examples of the method of shaping a collagen filament into a cotton-like substrate include a method of twining a collagen filament by stirring it in air or a liquid and a method of pulling out a collagen filament from a core member such as a bobbin around which the collagen filament has been wound. In particular, from a viewpoint of easy production of a three-dimensional shape, it is preferable to twine the collagen filament in liquid.

Stirring may be performed by operating a stirring bar by hand or by using a stirring apparatus or the like to rotate a magnetic stirrer by a rotating magnetic field. Such stirring places collagen filaments into a state where they tangle with each other, i.e., into a cotton-like substrate. As described above, the collagen filaments have already been subjected to crosslinking (crosslinking step), so the collagen filaments do not adhere to each other in such tangling state. That is, although the collagen filaments contact each other, if the collagen filaments are subjected to an external force, a contact site may shift or the collagen filaments may be separated from each other. In the present invention, such contact of collagen filaments is referred to as "non-adhered contact". When collagen filaments are shaped into a cotton-like substrate having a three-dimensional shape as described above, it may be used as a three-dimensional scaffold of cells for tissue remodeling. Meanwhile, appropriate holes are formed in the cotton-like substrate having a three-dimensional shape, so oxygen or the like necessary for cells or culture can easily enter into the three-dimensional shape. To form such holes, the specific volume of the cotton-like substrate is 1 to 100 $cm^3/g$, preferably 2 to 55 $cm^3/g$, and more preferably 4 to 12 $cm^3/g$.

Meanwhile, from a viewpoint that production steps may be reduced, the above-described stirring liquid is preferably a neutralizing solution. The neutralizing solution includes one to neutralize a solvent of a collagen solution and a washing solution to be used after neutralization, and there may be used an acidic solution, alkaline solution, etc. depending on the pH of the cotton-like substrate. The neutralization is preferably repeated at least twice while exchanging the neutralizing solution. In addition, as the neutralizing solution, a weak acidic solution or a weak alkaline solution is preferable from a viewpoint of maintaining a molecular structure of collagen, and for example, there may be used an aqueous sodium hydrogen carbonate solution, ammonia water, phosphate buffer, etc. Among them, the aqueous sodium hydrogen carbonate solution is preferable, but it is not obligatory. Neutralization may suppress an inflammatory response in implanting a collagen substrate in a living body, so it is preferable.

The above-described cotton-like substrate is desirable because it includes non-adhered contact sites where the above-described collagen filaments contact and do not adhere to each other and adhered contact sites where the collagen filaments adhere to each other, so it has an improved elasticity and a maintained three-dimensional structure. The term "adhere" means a state where collagen filaments bind together to the extent that a shear stress between the collagen filaments may be generated. Examples of the bond form include a bond by a physical interaction, a bond by a chemical interaction, and a mechanical bond. In particular, from a viewpoint of bond strength, a bond formed by a chemical interaction is preferable, but the present invention is not limited thereto. Examples of the bond formed by a chemical interaction include a covalent bond, an ionic bond, a coordinate bond, and a hydrogen bond. In particular, from a viewpoint of bond strength, the covalent bond and ionic bond are preferable, and the covalent bond is most preferable, but the present invention is not limited thereto. Examples of a method of forming a covalent bond mainly include a method by crosslinking.

As the above-described crosslinking, a physical crosslinking method and a chemical crosslinking method may be used as described above, but the physical crosslinking method is preferable from a viewpoint of safety in implantation in a living body and cytotoxicity. Meanwhile, in the case that thermal dehydration crosslinking is performed as a physical crosslinking method, it is preferably performed under reduced pressure at about 110 to 140° C. for about 6 to 48 hours. This treatment allows collagen filaments to partially adhere to each other. Although the collagen filaments have been crosslinked in the form of fibers by such crosslinking, their surfaces are slightly solved in liquid such as water. When the collagen filaments, which constitute the cotton-like substrate and are slightly solved, are subjected to crosslinking again, part of a non-adhered contact site is changed into an adhered contact site. That is, the collagen filaments partially adhere to each other by crosslinking. This treatment maintains the state where the above-described cotton-like substrate bends with twining and maintains a three-dimensional structure having continuous holes. Note that the above-described cotton-like substrate may be air-dried before or after the further crosslinking.

Meanwhile, in another embodiment, collagen filaments may be immersed in a neutralizing solution together with a core member before the collagen filaments are pulled out from the core member. However, it is necessary that the collagen filaments be previously subjected to crosslinking to make the filaments insoluble. The neutralizing solution includes one to neutralize a solvent of a collagen solution and a washing solution to be used after neutralization, and there may be used an acidic solution, alkaline solution, etc. depending on the pH of the collagen filaments. The neutralization is preferably repeated at least twice while exchanging the neutralizing solution. In addition, as the neutralizing solution, a weak acidic solution and a weak alkaline solution are preferable from a viewpoint of maintaining a molecular structure of collagen, and for example, there may be used an aqueous sodium hydrogen carbonate solution, ammonia water, phosphate buffer, etc. Among them, the aqueous sodium hydrogen carbonate solution is preferable, but the neutralizing solution is not limited thereto. Neutralization may suppress an inflammatory response in implanting a collagen substrate in a living body, so it is preferable.

While the above-described collagen filaments have been crosslinked by crosslinking, their surfaces are slightly solved in liquid such as water. When the collagen filaments, which are wound around a core member and are slightly solved by immersion in a neutralizing solution, are subjected to crosslinking again, part of non-adhered contact sites are changed into adhered contact sites. That is, the collagen filaments wound around the core member partially adhere to each other by crosslinking. After that, the collagen filaments are pulled out from the core member. The collagen filaments are not unraveled while rotating the core member, but the core member is pulled out in the direction of a rotating axis line while maintaining the state where the collagen filaments are wound around the core member. In this way, the collagen filaments may be pulled out from the core member while maintaining the above-described adhered contact sites formed by the further crosslinking. The collagen filaments pulled out from the core member have an almost cylindrical shape having a hollow corresponding to the core member. A flocculent three-dimensional structure having appropriate holes is formed by appropriately unraveling the collagen filaments with the cylindrical shape while maintaining the adhered contact sites. Note that the above-described cotton-like substrate may be air-dried before or after the further crosslinking.

As described above, a collagen substrate having a three-dimensional structure can be obtained. The cotton-like substrate formed of collagen filaments has a three-dimensional structure in which the filaments contact each other but has non-adhered contact sites. That is, it has contact sites where the collagen filaments do not adhere to each other. Therefore, when a compression force is imparted, the independent collagen filaments bend by sliding or releasing the contact sites, and the collagen substrate may be deformed so as to reduce the total volume of the collagen substrate. Meanwhile, when the compression force is removed from the substrate, the original shape is restored by the elasticity of the collagen filaments and the adhered contact sites.

Thus, a collagen substrate can be used as a substrate for medical applications and may be flexibly deformed depending on the shape of a defective portion or hemostasis portion in a living body. Meanwhile, in in vitro culture, tissue cells can be three-dimensionally cultured using the collagen substrate as a scaffold. In the case that a collagen substrate is used as a substrate for culture, an agent suitable for cell culture, such as laminin or fibronectin, can be impregnated in the collagen substrate. Meanwhile, a collagen substrate can be coated with such an agent.

Further, use of a collagen substrate as a hemostat provides a hemostat that has excellent handling ability without occurrence of loosening or the like and has a high hemostasis effect. In the case that a collagen substrate is used as a hemostat, the collagen substrate may be impregnated in or coated with an agent having a hemostasis effect.

Hereinafter, examples of the present invention will be described.

EXAMPLE 1

Figure 1:
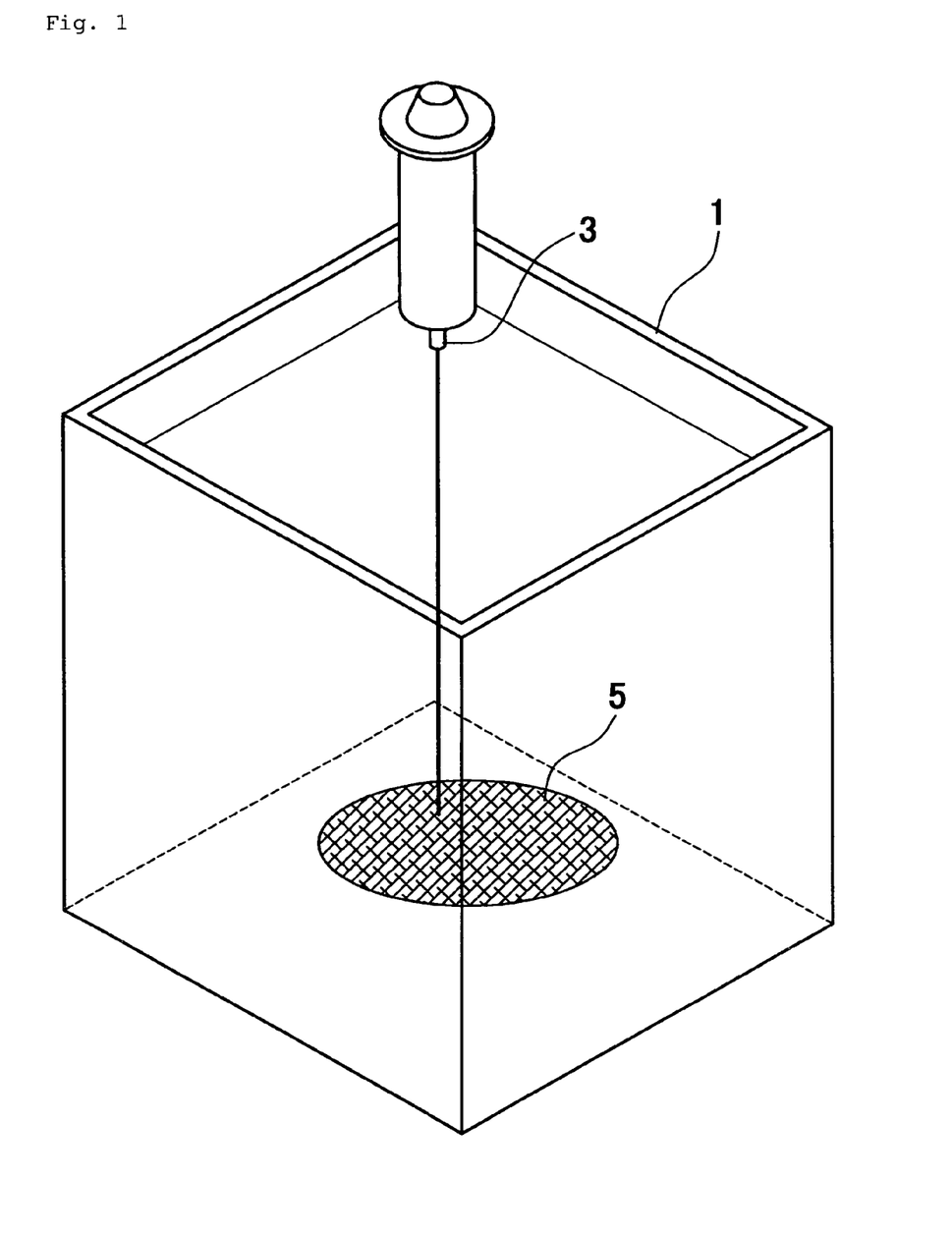
FIG. 1 shows a method of manufacturing a three-dimensional collagen mesh 5 in Example 1.

Collagen type I and type III mixed powders from a pig (manufactured by Nippon Meat Packers, Inc., SOFD type) were dissolved in distilled water for injection, to thereby prepare a 7 w/w % collagen solution. As shown in FIG. 1, 150 ml of the collagen solution was discharged from nozzle 3 into a coagulation bath 1 containing 3 L of 99.5 v/v % ethanol (Wako Pure Chemical Industries, Ltd., reagent chemicals). In this way, a three-dimensional structure was obtained.

Figure 2:
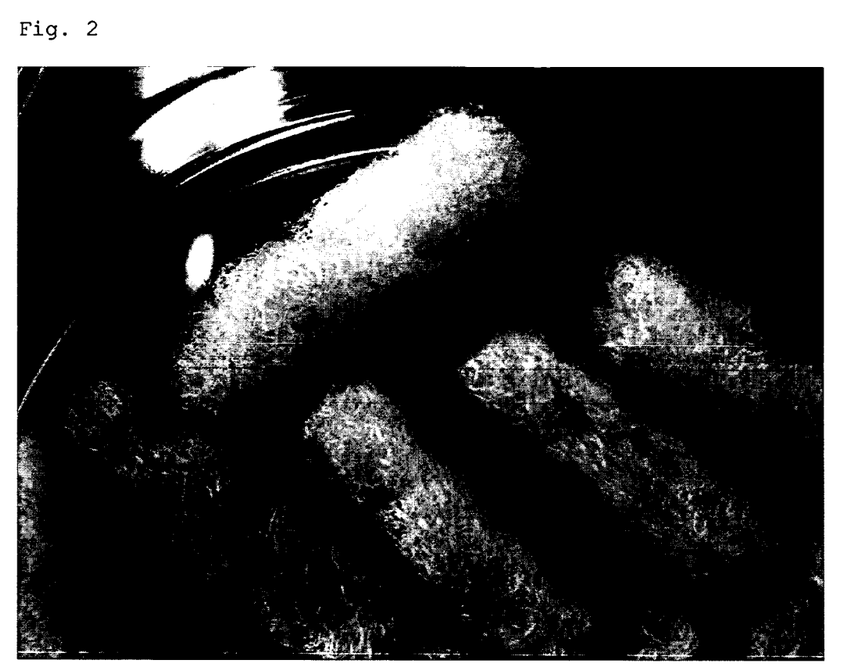
FIG. 2 shows a three-dimensional collagen mesh 5 obtained in Example 1.

The three-dimensional structure was air-dried in a clean work station, and was subjected to a thermal dehydration crosslinking reaction in a vacuum dry oven (manufactured by EYELA: VOS-300VD type) under high vacuum (1 torr or less) at 120° C. for 24 hours. After crosslinking, the three-dimensional collagen mesh 5 was subjected to neutralizing treatment for 30 minutes in an aqueous solution of 7.5 w/w % sodium hydrogen carbonate (baking soda). After neutralizing, the resultant was washed with pure water, and air-dried in the clean work station again. And then the three-dimensional collagen mesh 5 was subjected to thermal dehydration crosslinking reaction in a vacuum dry oven (manufactured by EYELA: VOS-300VD type) under high vacuum (1 torr or less) at 120° C. for 24 hours again. In this way, a collagen substrate was obtained as shown in FIG. 2.

EXPERIMENTAL EXAMPLE 1

(Culture Experiment)

Three-dimensional culture of human chondrocytes was carried out using the collagen substrate manufactured in Example 1. The collagen substrate was molded into the shape of an ear. First, a cell suspension having a cell concentration of $4.0 \times 10^5$ cells/ml was prepared using a medium obtained by adding 10 ml of Chondrocyne Growth Supplement (product name, manufactured by CELL APPLICATIONS) to 500 ml of Chondryocyne Basal Medium (product name, manufactured by CELL APPLICATIONS). Next, 0.3 ml of the above-mentioned cell suspension was applied onto part of the collagen substrate (about 0.15 g). The collagen substrate was left to stand in a petri dish (manufactured by CORNING, 48 wells) so that a portion where the cell suspension was applied was on the bottom of the dish, and 0.6 ml of the above-motioned medium was gently poured and static culture was carried out for 2 months. Culture was carried out at 37° C. in a 5 v/v % $CO_2$ atmosphere, and the medium was exchanged every 2 days.

Figure 3:
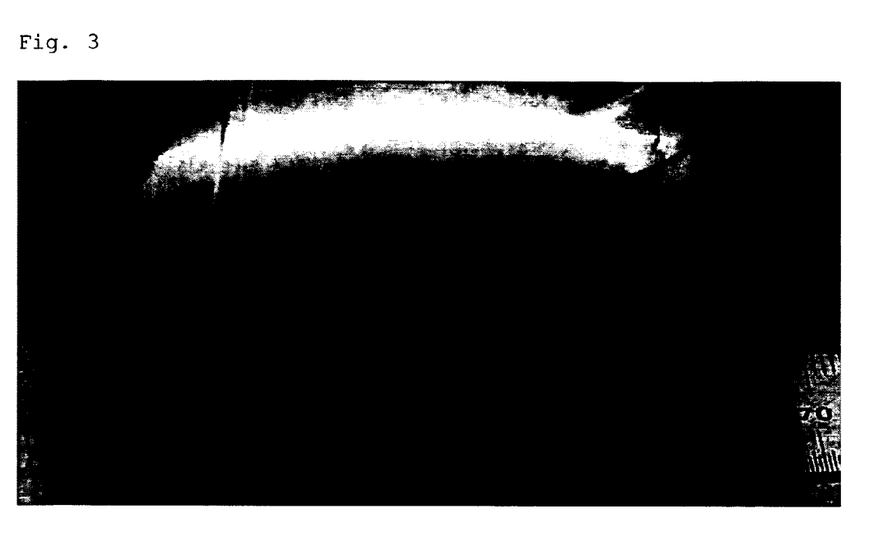
FIG. 3 shows human chondrocytes cultured in Experimental Example 1.

After 2 months from the initiation of culture, the state of the collagen substrate was observed (FIG. 3). It was confirmed that the cells inoculated onto the basal plane grew in three dimensions into nearly the same shape as that of the collagen substrate before inoculation. Thus, the shape closely resembled the shape of an ear. The results confirmed that the collagen substrate according to the present invention is a substrate for culture that may contribute to future regenerative medicine.

EXAMPLE 2

Figure 4:
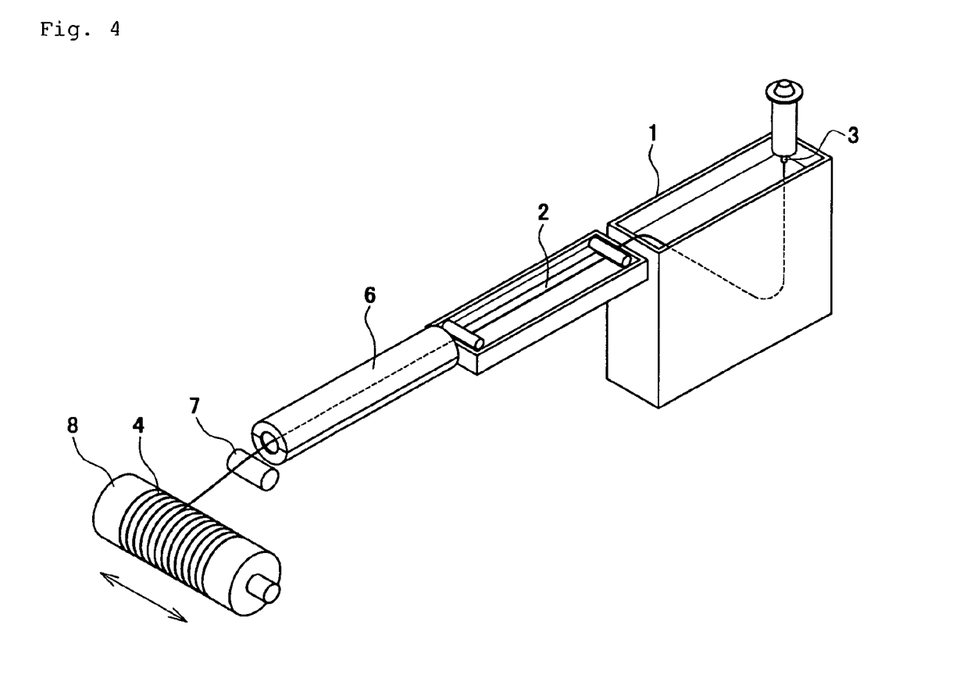
FIG. 4 shows a configuration of a production apparatus for the collagen filaments 4 in Example 2.

Collagen type I and type III mixed powders from a pig (manufactured by Nippon Meat Packers, Inc., SOFD type) was dissolved in distilled water for injection, to thereby prepare a 7 w/w % collagen solution. As shown in FIG. 4, 150 ml of the collagen solution was discharged into a coagulation bath 1 containing 3 L of 99.5 v/v % ethanol (Wako Pure Chemical Industries, Ltd., reagent chemicals). The collagen filaments pulled out from the coagulation bath 1 were immersed into a dehydration bath 2 that was provided separately from the coagulation bath 1 and filled with 99.5% ethanol. The collagen filaments 4 pulled out from the dehydration bath 2 were passed through an air dryer 6 for about 3 seconds and were then wound up using, as a core member, a roll-like wind-up tool 8 made of stainless-steel with a diameter of 78 mm and an overall length of 200 mm which was allowed to rotate at about 35 rpm, while a tension was maintained with a tension pulley 7 to prevent the collagen filaments 4 from loosening. In winding up the collagen filaments 4, the roll-like wind-up tool 8 was reciprocatingly moved at a speed of 1.5 mm/s in the axis direction of the roll-like wind-up tool 8.

Figure 5:
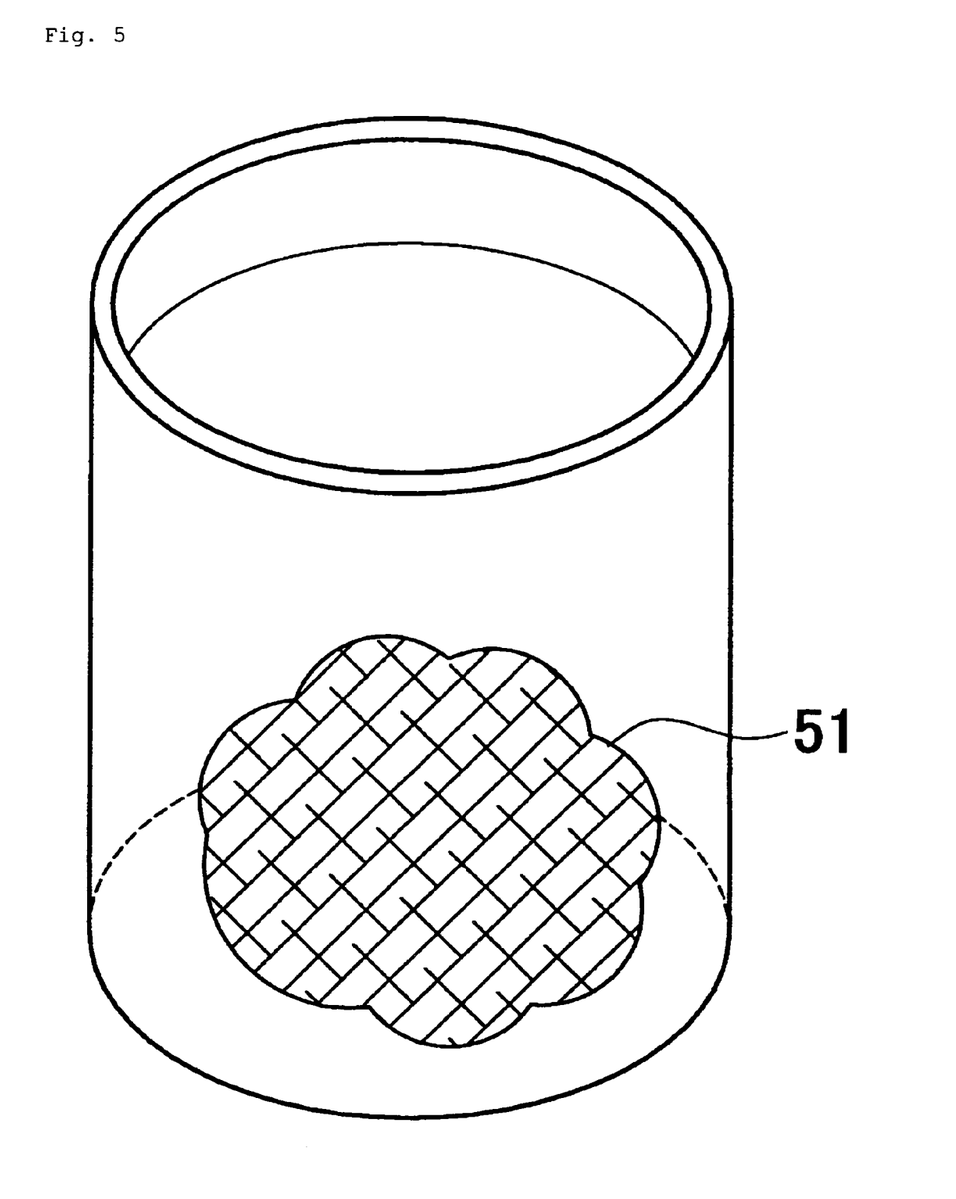
FIG. 5 shows a cotton-like substrate after a stirring step in Example 2.
Figure 6:
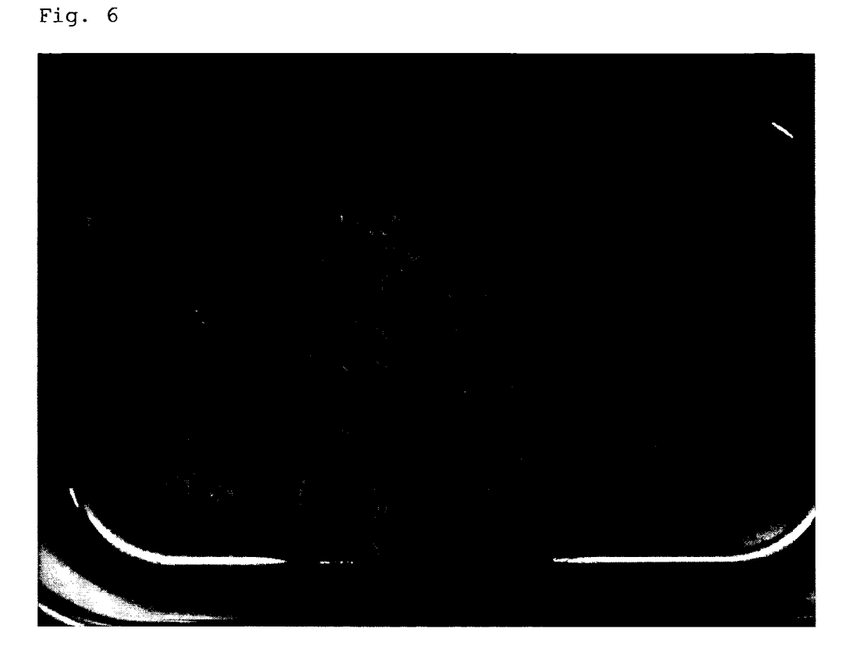
FIG. 6 shows a flocculent collagen substrate (cotton-like substrate) 51 obtained in Example 2.

The resultant collagen filaments 4 were subjected to a thermal dehydration crosslinking reaction in the state of being wound up around the wind-up tool 8 in a vacuum dry oven (manufactured by EYELA: VOS-300VD type) under high vacuum (1 torr or less) at 120° C. for 24 hours. Next, the collagen filaments 4 were taken out from the wind-up tool 8 and were subjected to neutralizing treatment for 30 minutes in an aqueous solution of 7.5 w/w % sodium hydrogen carbonate (baking soda) while stirring at a stirring speed of 1,000 rpm as shown in FIG. 5. In this way, a cotton-like substrate 51 made of the collagen filaments 4 was obtained. After neutralization, the cotton-like substrate 51 was washed with distilled water and air-dried in a clean bench. After that, the cotton-like substrate 51 was subjected to a thermal dehydration crosslinking reaction again in a vacuum dry oven under high vacuum (1 torr or less) at 120° C. for 12 hours. In this way, a collagen substrate was obtained as shown in FIG. 6.

EXPERIMENTAL EXAMPLE 2

(Culture Experiment)

Three-dimensional culture of human chondrocytes was carried out using the collagen substrate (comprised of collagen cotton-like substrate 51) manufactured in Example 2. First, a cell suspension having a cell concentration of $4.0 \times 10^5$ cells/ml was prepared using a medium obtained by adding 10 ml of Chondrocyne Growth Supplement (product name, manufactured by CELL APPLICATIONS) to 500 ml of Chondryocyne Basal Medium (product name, manufactured by CELL APPLICATIONS). Next, 0.3 ml of the above-mentioned cell suspension was applied onto part of the cotton-like substrate 51 (about 0.15 g). The collagen substrate was left to stand in a petri dish (manufactured by CORNING, 48 wells) so that a portion where the cell suspension was applied was on the bottom of the dish, and 0.6 ml of the above-mentioned medium was gently poured and static culture was carried out for 2 months. Culture was carried out at 37° C. in a 5 v/v % $CO_2$ atmospheres, and the medium was exchanged every 2 days.

Figure 7:
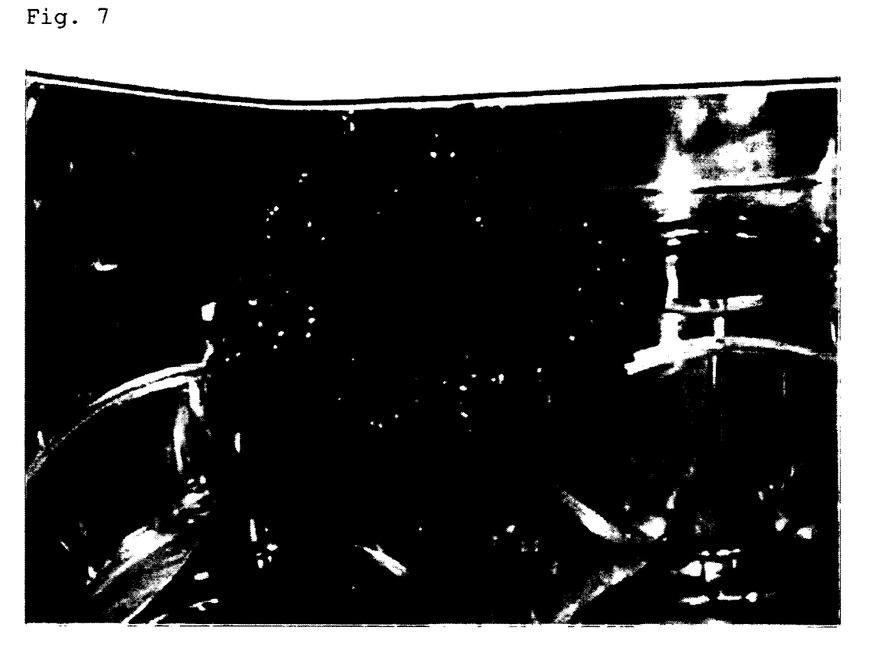
FIG. 7 shows human chondrocytes cultured in Experimental Example 2.

After 2 months from the initiation of culture, the state of the collagen substrate was observed (FIG. 7). It was confirmed that the cells inoculated onto the base of the substrate grew in three dimensions into nearly the same shape as that of the collagen substrate before inoculation. The results confirmed that the collagen substrate according to the present invention is a substrate for culture that may contribute to future regenerative medicine.

EXPERIMENTAL EXAMPLE 3

(Hemostasis Experiment)

Figure 8:
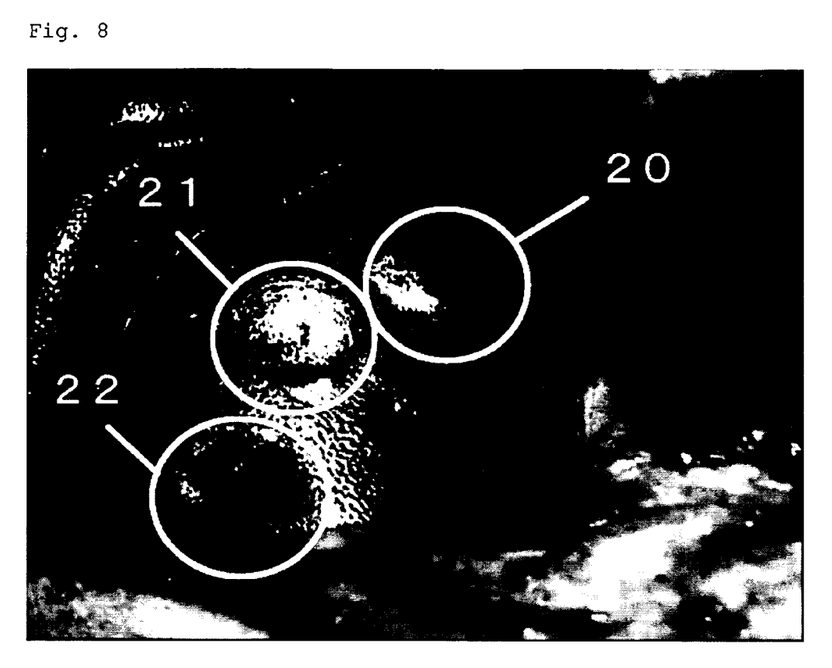
FIG. 8 shows a liver surface after hemostasis performed by surface compressions of superficial wounds in Experimental Example 3 with the flocculent collagen substrate (cotton-like substrate) 51 of Example 2, a hemostat of Comparative Example 1, and a hemostat of Comparative Example 2.

A hemostasis experiment was performed by surface compression of superficial wounds using the collagen substrate manufactured in Example 2. In Comparative Example 1, there was used a hemostat formed of oxycellulose (Surgical, imported and sold by: Johnson & Johnson K.K.), while in Comparative Example 2, there was used a hemostat formed of collagen (Integran, sold by: Nippon Zoki Pharmaceutical Co., Ltd., manufactured by: Koken Co., Ltd.). An incision was made in the abdomen of a beagle dog (female) to expose the liver using a surgical knife. Next, in three parts in the liver, superficial wounds each having a length of about 1 cm and a depth of about 0.1 cm were made in the same way. On the wounds in the three parts, the collagen substrate according to Example 2, the hemostat of Comparative Example 1, and the hemostat of Comparative Example 2 were separately put, and the collagen substrate and hemostats were pressed with medical gauze to perform abstrictions. The abstrictions were performed for about 1 minute, and then the states of hemostasis in the wounds were visually observed. The observed states are shown in FIG. 8. In FIG. 8, the wound where hemostasis was achieved with the collagen substrate according to Example 2 is denoted by reference numeral 20, the wound where hemostasis was achieved with the hemostat of Comparative Example 1 is denoted by reference numeral 21, and the wound where hemostasis was achieved with the hemostat of Comparative Example 2 is denoted by reference numeral 22.

EXPERIMENTAL EXAMPLE 4

(Hemostasis Experiment)

Figure 9:
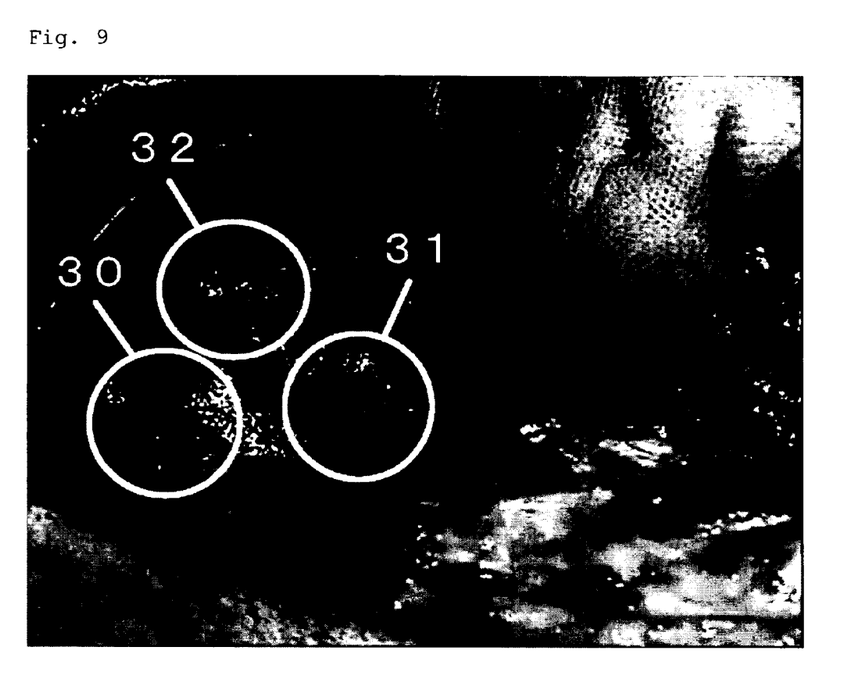
FIG. 9 shows a liver surface after hemostasis performed by surface compressions of deep wounds in Experimental Example 4 with the flocculent collagen substrate (cotton-like substrate) 51 Example 2, the hemostat of Comparative Example 1, and the hemostat of Comparative Example 2.

A hemostasis experiment was performed by inserting the hemostats into deep wounds using the collagen substrate manufactured in Example 2, the hemostat of Comparative Example 1, and the hemostat of Comparative Example 2. An incision was made in the abdomen of a beagle dog (female) to expose the liver using a surgical knife. Next, in three parts in the liver, deep wounds each having a length of about 2 cm and a depth of about 0.7 cm were made in the same way. The blood spilt out from the wounds was wiped off with medical gauze, and then the three wounds were respectively stuffed with the collagen substrate according to Example 2, the hemostat of Comparative Example 1, and the hemostat of Comparative Example 2. After that, the collagen substrate and the hemostats were pressed with medical gauze to perform abstrictions. The abstrictions were performed for about 1 minute, and then the states of hemostasis in the wounds were visually observed. The observed states are shown in FIG. 9. In FIG. 9, the wound where hemostasis was achieved with the collagen substrate according to Example 2 is denoted by reference numeral 30, the wound where hemostasis was achieved with the hemostat of Comparative Example 1 is denoted by reference numeral 31, and the wound where hemostasis was attempted with the hemostat of Comparative Example 2 is denoted by reference numeral 32.

Table 1 shows the observation results of the above-described Experimental Examples 2 and 3. To evaluate the respective Experimental Examples, the states of hemostasis in the wounds were visually observed and judged as three levels of "o", "?", and "x" shown below. Note that "-" indicates that operations for hemostasis could not be performed and evaluated.

TABLE 1

|  | Example 2 | Comparative Example 1 | Comparative Example 2 |
|---|---|---|---|
| Experimental Example 2 | o | x | o |
| Experimental Example 3 | o | o | — | o: Hemostasis was completely achieved
?: Hemostasis was not completely achieved, but bleeding was reduced
x: Bleeding was hardly reduced
—: Operations for hemostasis could not be performed It was confirmed that the collagen substrate manufactured in Example 2 could completely achieve hemostasis in wounds both in the case of hemostasis performed by compressing the surfaces of superficial wounds (Experimental Example 2) and in the case of hemostasis performed by inserting the hemostat into deep wounds (Experimental Example 3). Meanwhile, collagen is decomposed and absorbed in a living body, so the collagen substrate is not required to be removed from the wounds after hemostasis. Moreover, collagen has a hemostasis effect, so it is suggested that the collagen substrate is preferable as a hemostat.

In the case of hemostasis performed by surface compression of superficial wounds, the hemostat of Comparative Example 1 could hardly reduce bleeding at the wound. On the other hand, in the case of hemostasis performed by inserting the hemostat into deep wounds, hemostasis was completely achieved at the wounds. However, the hemostat of Comparative Example 1 is made of cellulose, so it is necessary to remove the hemostat from the wounds after hemostasis. Although not shown in Experimental Example 4, it is suggested that bleeding may occur again at the wounds in the removing operation.

In the case of hemostasis performed by surface compression of superficial wounds, the hemostat of Comparative Example 2 could completely achieve hemostasis at the wounds. On the other hand, in the case of hemostasis performed by inserting it into deep wounds, the hemostat was hard to handle due to adhesion of the hemostat to the fingertips, tweezers, etc., and the hemostat could not be inserted into the wounds, so it was impossible to perform the operation for hemostasis.

As described above, both in the case of hemostasis performed by surface compression of superficial wounds and in the case of hemostasis performed by inserting the collagen substrate into deep wounds, the flocculent collagen substrate according to the present invention was shown to completely achieve hemostasis at the wounds and to have excellent handling ability in the operation for hemostasis.

This application claims priority of Japanese Patent Application Nos. 2005-199218, 2005-199344 and 2005-289300 filed July 7, July 7 and Sep. 30, 2005, respectively, which are incorporated herein by reference.

What is claimed is:

1. A method of manufacturing a collagen substrate comprising:
   (1) spinning collagen into collagen filaments;
   (2) crosslinking the collagen filaments;
   (3) stirring the crosslinked collagen filaments in a liquid to form a three-dimensional mesh; and
   (4) drying the three-dimensional mesh and obtaining the collagen substrate.

2. The method of manufacturing the collagen substrate according to claim 1, wherein collagen in step (1) is dissolved in a solvent and the liquid is a solution for neutralizing the solvent.

3. The method of manufacturing the collagen substrate according to claim 1, wherein further crosslinking is performed after stirring the collagen filaments in the liquid.

4. The method of manufacturing the collagen substrate according to claim 1, comprising spinning the collagen into collagen filaments having a length of 100 mm or more.

5. The method of manufacturing the collagen substrate according to claim 4, wherein collagen in step (1) is dissolved in a solvent and the liquid is a solution for neutralizing the solvent.

6. The method of manufacturing the collagen substrate according to claim 4, wherein further crosslinking is performed after stirring the collagen filaments in the liquid.

* * * * *